United States Patent [19]

Mueller et al.

[11] Patent Number: 5,064,860
[45] Date of Patent: Nov. 12, 1991

[54] METHOD OF INHIBITING SUPEROXIDE GENERATION

[75] Inventors: Richard A. Mueller, Glencoe; Akira Nakao, Skokie; Richard A. Partis, Evanston, all of Ill.

[73] Assignee: G. D. Searle & Co., Chicago, Ill.

[21] Appl. No.: 579,138

[22] Filed: Sep. 7, 1990

[51] Int. Cl.$^5$ ............................................. A61K 31/19
[52] U.S. Cl. ................................................. 514/568
[58] Field of Search ........................................ 514/568

[56] References Cited

U.S. PATENT DOCUMENTS

| | | | |
|---|---|---|---|
| 4,621,098 | 11/1986 | Umminger et al. | 514/562 |
| 4,711,903 | 12/1987 | Mueller et al. | 514/381 |
| 4,755,524 | 7/1988 | Mueller et al. | 514/381 |

FOREIGN PATENT DOCUMENTS 0131221  1/1985  European Pat. Off. .

OTHER PUBLICATIONS

Cross, C. E., et al., "Oxygen Radicals and Human Disease," Ann. Int. Med., 107:526–545 (1987).
Ward, P. A., "Oxygen Radicals, Inflammation, and Tissue Injury," Free Radical Biology & Medicine, 5:403–408 (1988).
Shepard, V. L., "The Role of the Respiratory Burst of Phagocytes in Host Defense," Semin. Respir. Infect., 1(2):99–106 (1986).
Kukreja, R. C., et al., "PGH Synthase and Lipoxygenase Generate Superoxide in the Presence of NADH or NADPH," Circulation Research 59(6):612–619 (1986).
Katayama, K., et al., Agents and Actions, 21(3/4):269–271 (1987).
Biemond, P., et al., Scand. J. Rheumatology, 19:151–156 (1990).
Kreutner, W., et al., J. Pharmacol. Exp. Ther., 247(3):997–1003 (1988).
Cencetti, A., et al., Clinical Rheumatology, 9(1):51–55 (1990).
Auer, D. E., et al., J. Vet. Pharmacol. Therap., 13(1):59–66 (1990).
Kanofsky, J. R., Chem. Biol. Interactions, 70:1–28 (1989).

*Primary Examiner*—Stanley J. Friedman
*Attorney, Agent, or Firm*—Mary Jo Kanady; Paul D. Matukaitis

[57] ABSTRACT

The present invention relates to a method of inhibiting superoxide generation which comprises administering to a mammal in need of such treatment an amount of a compound of the Formula I

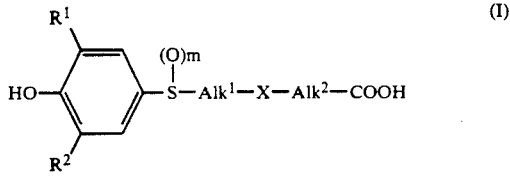

wherein $R^1$ and $R^2$ are the same or different and independently represent tert-alkyl or phenyl; $Alk^1$ represents straight or branched chain alkylene of 1 to 10 carbon atoms, X represents sulfur or oxygen, $Alk^2$ represents straight or branched chain alkylene of 1 to 4 carbon atoms; and m is 0, 1 or 2; or a pharmaceutically acceptable salt or stereoisomer or geometric isomer thereof, which is effective to inhibit superoxide generation.

9 Claims, No Drawings

METHOD OF INHIBITING SUPEROXIDE GENERATION

BACKGROUND OF THE INVENTION

1. Field of the Invention

The present invention is directed to a method of inhibiting superoxide generation using phenolic thioether acids which inhibit the generation of superoxide.

2. Background Information and Related Art

Recently, oxygen radicals have been implicated in the pathogenesis of many diseases. This implication is reflected by the many conferences devoted to this topic, books on the subject of free radicals and disease, and the appearance of two new specialized journals: *Free Radical Research Communications*, and *Free Radical Biology and Medicine*.

Much is known about the physicochemical properties of the various oxygen radicals, but knowledge of their overall importance in the initiation and amplification of human disease is limited. Some clinical conditions in which oxygen radicals are thought to be involved are discussed in Cross, C. E., et al., "Oxygen Radicals and Human Disease," ANN. INT. MED., 107:526-545 (1987) (see Table 1, p. 527) and Ward, P. A., et al., "Oxygen Radicals, Inflammation, and Tissue Injury," FREE RADICAL BIOLOGY & MEDICINE, 5:403-408 (1988). Among the clinical conditions in which oxygen radicals are thought to be involved are, for example, inflammatory-immune injury, autoimmune diseases, ischemia-reflow states, aging disorders, cancer, cigarette-smoke effects, emphysema, acute respiratory distress syndrome (ARDS), atherosclerosis, rheumatoid arthritis, senile dementia, cataractogenesis, retinopathy of prematurity, radiation injury and contact dermatitis.

Oxygen radicals are capable of reversibly or irreversibly damaging compounds of all biochemical classes, including nucleic acids, protein and free amino acids, lipids and lipoproteins, carbohydrates, and connective tissue macromolecules. These species may have an impact on such cell activities as membrane function, metabolism, and gene expression. Oxygen radicals are formed in tissues by many processes (see Cross, et al., p. 528, Table 2). These are believed to be both endogenous, such as mitochondrial, microsomal and chloroplast electron transport chains; oxidant enzymes such as xanthine oxidase, indoleamine dioxygenase, tryptophan dioxygenase, galactose oxidase, cyclooxygenase, lipoxygenase, and monoamine oxidase; phagocytic cells such as neutrophils, monocytes and macrophages, eosinophils, and endothelial cells; and antioxidation reactions; and exogenous, such as redoxcycling substances, drug oxidations, cigarette smoke, ionizing radiation, sunlight, heat shock and substances that oxidize glutathione. They may be involved in the action of toxins such as paraquat, cigarette smoke, and quinone antitumor drugs.

Various thioether compounds have been described previously. For example, U.S. Pat. No. 4,711,903 and its continuation-in-part, U.S. Pat. No. 4,755,524 disclose compounds of the formula

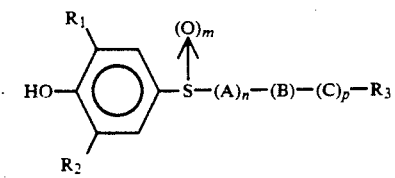

wherein: $R_1$ and $R_2$ are the same or different and independently represent tert-alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, substituted phenyl or substituted benzyl; C represents methylene or methylene substituted by alkyl; $R_3$ represents $CO_2H$, $CO_2$-alkyl or a tetrazole group; m is 0 or 1, n is 2, 3 or 4 and p is 1, 2 or 3; and the pharmaceutically acceptable salts thereof. The compounds are specific inhibitors of 5-lipoxygenase and are useful in the treatment of local and systematic inflammation, allergy and hypersensitivity reactions and other disorders in which agents formed in the 5-lipoxygenase metabolic pathway are involved. There is no disclosure of superoxide inhibiting activity.

European Patent Application publication No. 0131221 discloses compounds of the formula

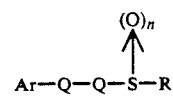

in which Ar is phenyl or phenyl substituted by one to three of varied substituents, for example, alkyl, alkoxy, hydroxy, etc.; Q is oxygen, sulfur or an NH group; A is straight or branched chain, optionally substituted, alkylene and R is hydrogen or straight or branched alkyl, optionally substituted by alkoxy, hydroxyl, carboxyl, alkoxycarbonyl, etc.; and n is 0, 1 or 2. The disclosed compounds are indicated to have anti-inflammatory and anti-allergic properties through inhibition of undefined anaphylactic and anaphylactoid reactions, although no test data are provided. The preferred compounds are stated to be those in which Q represents oxygen and n is 0 without mention of any preference among the numerous possible substituents for R or substituted phenyl as Ar. In contrast to the invention disclosed in EPA 0131221, the compounds used in the method of the present invention all have a sulfur atom at the position corresponding to Q as well as having di(tertiary)-alkyl or diphenyl groups as substituents on the phenol moiety corresponding to the substituted Ar group in the above publication which, as described therein, may or may not comprise a phenol. The compounds of Formula I of the present invention, including their surprising specific superoxide inhibitory properties, are, therefore, not specifically described in EPA 0131221.

SUMMARY OF THE INVENTION

The present invention relates to a method of inhibiting superoxide generation which comprises administering to a mammal in need of such treatment an amount of a compound of the Formula I

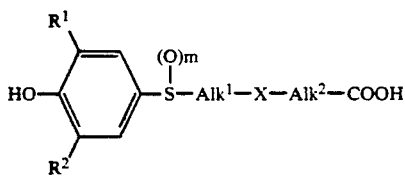

(I)

wherein $R^1$ and $R^2$ are the same or different and independently represent tert-alkyl or phenyl; $Alk^1$ represents straight or branched chain alkylene of 1 to 10 carbon atoms, X represents sulfur or oxygen, $Alk^2$ represents straight or branched chain alkylene of 1 to 4 carbon atoms; and m is 0, 1 or 2; or a pharmaceutically acceptable salt or stereoisomer or geometric isomer thereof, which is effective to inhibit superoxide generation.

The compounds of Formula I are inhibitors of superoxide generation in neutrophils and are useful in the therapeutic or prophylactic treatment of disease conditions which are mediated wholly or partly by superoxide generation such as adult respiratory distress syndrome, superoxide mediated inflammatory or allergic conditions, and other medical conditions which are caused by or aggravated by superoxide.

Although it has been speculated that 5-lipoxygenase may be involved in superoxide generation, Applicants have discovered that superoxide generation is not governed by 5-lipoxygenase. Thus the activity of the compounds of Formula I in inhibiting superoxide generation is not related to the ability to inhibit 5-lipoxygenase.

DETAILED DESCRIPTION OF THE INVENTION

The present invention also relates to a method of inhibiting superoxide generation which comprises administering to a mammal in need of such treatment an amount of a compound of the formula

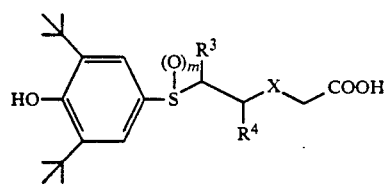

(II)

wherein $R^3$ and $R^4$ are alike or different and are hydrogen or alkyl of 1 to 4 carbon atoms, X is sulfur or oxygen, and m is 0, 1 or 2; or a pharmaceutically acceptable salt or stereoisomer or geometric isomer thereof which is effective to inhibit superoxide generation.

The term "tert -alkyl" as used herein in reference to $R_1$ and $R_2$ refers to branched chain alkyl moieties of from about 4 to 10 carbon atoms having a tertiary carbon atom attached to the phenyl ring substituted by $R_1$ and $R_2$. Examples of such groups are tert-butyl, i.e., 1,1-dimethylethyl, 1-1-dimethylpropyl, 1-methyl-1-(ethyl)-pentyl, 1,1-diethylpropyl, 1-ethyl-1-(propyl)butyl and the like.

The term "alkylene" refers to straight or branched chain alkylene groups having between about 1 to 10 carbon atoms including, for example, methylene, ethylene, propylene, 1,2-dimethylethylene, pentylene, 1-methylbutylene, isopentylene, neopentylene, etc.

The term "alkyl" refers to straight or branched chain alkyl radicals having about 1 to 4 carbon atoms including methyl, ethyl, propyl, isopropyl, butyl, t-butyl, etc.

Particularly preferred compounds of Formula I are those wherein $R_1$ and $R_2$ are both tert-alkyl.

Also preferred for use in the invention are compounds and isomers of the formula

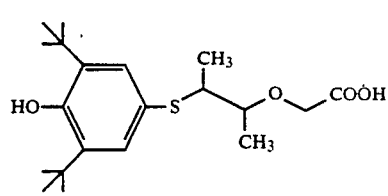

(III)

The expression "pharmaceutically acceptable salts" is intended to include those salts capable of being formed with the compounds of the present invention without materially altering the chemical structure or pharmacological properties thereof. Such salts include inorganic and organic cations or acid addition salts, such as sodium, potassium, calcium, ammonium, alkylammonium, triethanolamine, lysine, hydrochloric, hydrobromide, etc. well known to those skilled in the art. The foregoing salts are prepared in the conventional manner by neutralization of the compounds of Formula I with the desired base or acid.

The compounds of the present invention can be administered in such oral dosage forms as tablets, capsules, pills, powders, granules, elixirs, or syrups as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but nontoxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the particular condition. The effective amount for administration is ordinarily that amount which is required to assure that the mammalian neutrophils involved in the generation of superoxide will be exposed to a sufficient concentration of drug to inhibit the generation of superoxide. A dosage regimen can be effectively determined for each patient or animal by initial intravenous infusion at a low dosage level, e.g., 0.01 µg/kg/min and thereafter increasing the dosage until the desired effect is obtained. Thereafter, oral dosages can be determined which will yield equivalent blood levels of drug. Dosages of the compounds of the present invention, will range generally between about 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered transdermally or topically to treat proliferative skin conditions such as psoriasis. The daily dosage may be administered in a single dose or in equal divided doses three or four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds used in practicing the invention may be prepared as described in U.S. Pat. Nos. 4,711,903 and 4,755,524 both of which are incorporated herein by reference.

In addition, compounds of Formula I in which X is oxygen, and Alk$^2$ is methylene may be prepared as described in the following reaction scheme.

SCHEME A

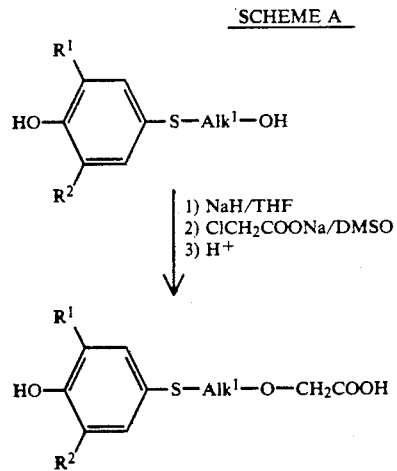

BIOLOGICAL EVALUATIONS

The compounds of the invention are evaluated with respect to 5-lipoxygenase inhibition according to the following assay procedure.

Inhibition of 5-lipoxygenase, in vitro:
anti-inflammatory, anti-allergy activities.

The 100,000×g supernatant fraction of Rat Basophilic Leukemia Cell Homogenate (RBL-1) serves as a 5-lipoxygenase enzyme source. The enzyme is incubated with [1-$^{14}$C]-arachidonic acid and Ca++ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the IC$_{50}$ value (inhibitory concentration to inhibit 50%).

The compounds of the invention are evaluated with respect to superoxide modulating activity according to the following assay procedure:

Human neutropil suproxide generation: Superoxide generation by formyl-methionyl-leucyl-phenylalanine (FMLP)-stimulated neutrophils was quantitated by the reduction of cytochrome C (Badwey, J. A., Curnutte, J. T. and Karnovsky, M. L., cis-Polyunsaturated fatty acids induce high levels of superoxide production by human neutrophils. *J. Biol. Chem.* 256: 12640–12643, 1981.) To 5 million neutrophils in 2.85 ml of Krebs-Ringer phosphate buffer, pH 7.2, 50 $\mu$l of inhibitor (in 10% DMSO/buffer), and 50 ul ferricytochrome C (5 mM, stock) were added and preincubated for 3 minutes at 37° C. Absorption measurements at 550 nm were recorded at start of preincubation. Fifty ul FMLP (6 uM, stock) was added to initiate reaction. A plateau was reached within 3 minutes and this reading—initial reading (before addition of FMLP) was used to calculate nanomoles of superoxide generated based on a molar extinction coefficient of $2.1 \times 10^4$ cm$^{-1}$mole$^{-1}$.

Isolation of human neutrophils: Human neutrophils were isolated from freshly drawn blood of healthy donors. Two ml of 5% dextran (MW 200,000–300,000) in saline was added to 10 ml aliquots of blood, mixed and placed upright for 45 min. at 37° C. Approx. 8–10 ml of the plasma-white cell suspension from the dextran sedimentation was layered on 3 ml of Ficol-paque in a ml tube and centrifuged at 400 g for 30 min. The supernate, containing plasma and platelets, was discarded by aspiration, and the pellet, containing predominantly neutrophils, was resuspended in 1 ml saline. The suspension was transferred to a clean tube, and pooled with other aliquots of blood treated similarly. The pooled suspension was centrifuged at 350 g for 5 min. and supernate discarded. The pellet was resuspended in 5 ml of 0.05% NaCl with a plastic Pasteur pipette for 25 seconds to lyse contaminating red cells, then 5 ml of 1.75% NaCl added to regain isotonicity. The red cell lysing procedure was repeated, the cells suspended in appropriate buffer (depending on assay) and counted.

For comparison the compound of Formula IV, a known 5-lipoxygenase inhibitor described in U.S. Pat. No. 4,663,333, was used.

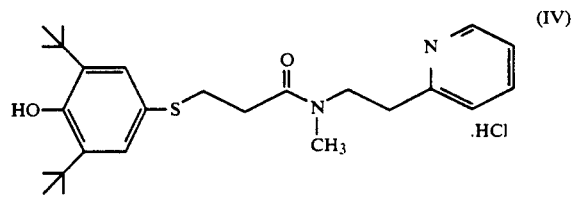

The results with respect to certain compounds of the present invention are set forth in Table I below.

TABLE 1

| Compound Example Number | 5-Lipoxygenase Inhibition $IC_{50}$ (μM) | Inhibition of FMLP Induced Superoxide $IC_{50}$ (μM) |
| --- | --- | --- |
| 9, 11 | 4.9 | 11 |
| 18 | 3.5 | 10 |
| 17 | 4.3 | 10 |
| 4, 5 | 3.3 | 5 |
|  | 1.4 |  |
| 12 | 12% inhibition at 100 μM | ~50 |
| 13 | 4% inhibition at 100 μM | ~30 |
| Formula IV (Comparison) | 0.32 | Stimulates superoxide generation |

The compound of Formula IV inhibited 5-lipoxygenase, but it did not inhibit superoxide generation. Instead it stimulated superoxide generation. At 5 μm it induced the neutrophils to increase superoxide by 50% and at 10 μm the compound of Formula IV induced a 227% increase in superoxide generated. This data indicates that superoxide generation is not dependent on 5-lipoxygenase and that the ability of a compound to inhibit 5-lipoxygenase is not predictive of its ability to inhibit superoxide generation.

Complement C5a induced superoxide generation is also inhibited by compounds of the present invention.

The following non-limiting examples further illustrate details for the preparation of the compounds used in practicing the present invention. Those skilled in the art will readily understand and appreciate that known variations of the conditions and procedures in the following preparative methods can be utilized. All temperatures are degrees Celcius unless otherwise noted. Melting points were determined on a Thomas-Hoover melting point apparatus and are uncorrected.

EXAMPLE 1
1—3,5-bis(1,1-dimethylethyl)-4-hydroxyphenyl thiocyanate

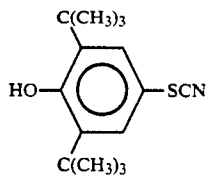

To a three-necked, round bottom 5 L flask, equipped with a mechanical stirrer, gas inlet, thermometer and gas outlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1 and ½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated by addition of water, filtered and dried for 2 days over phosphorous pentoxide. The resulting gummy yellow solid was recrystallized from pentane and dried in vacuo to yield the product as a white powder, m.p. 61.5°-63° C.

Analysis calc. for $C_{15}H_{21}NSO$:Theory: C, 68.40; H, 8.03; N, 5 32; S, 12.17.Found: C, 68.85; H, 8.05; N, 5.29; S, 12.12.

EXAMPLE 2
2—2,6-bis(1,1-dimethylethyl)-4-mercaptophenol

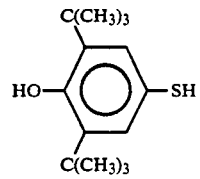

3,5-bis(1,1-Dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product.

EXAMPLE 3
3—[[2-[[3,5-bis(1,1-dimethylethyl)-4-hydroxyphenyl]-thio]ethyl]thio]acetic acid, monosodium salt

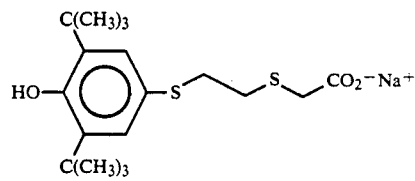

Mercaptoacetic acid (1.3 g, 0.0144 mole) was added to a solution of sodium ethoxide, prepared from sodium (0.66 g, 0.0288 mole) in ethyl alcohol (25 ml). After stirring for one hour, 1-bromo-2-chloroethane (6 ml, 0.072 mole) was added all at once and the solution stirred for 2 hours. After refluxing for 4 hours, the excess 1-bromo-2-chloro ethane was removed by rotary evaporator. Ethyl alcohol (50 ml) was added to the residue and the sodium salt of 2,6-bis 1,1-dimethylethyl)-4-mercaptophenol prepared from sodium (0.33 g, 0.0144 mole) and 2,6-bis(1,1-dimethylethyl)-4-mercaptophenol (3.43 g, 0.0144 mole) in ethyl alcohol (25 ml) was added by cannula. After stirring for eighteen hours at room temperature, the mixture was refluxed for 1 hour, cooled to room temperature and water (50 ml) added with rapid stirring. The ethyl alcohol was removed with a rotary evaporator. The aqueous residue was extracted with ethyl acetate (2×100 ml) combined, dried over sodium sulfate, filtered and concentrated. The residue was crystallized from ethyl acetate/hexane. This solid was recrystallized from ethyl acetate/hexane to give the title compound.

Analysis calc. for $C_{18}H_{27}O_3S_2Na$ (378.54):Calc.: C, 57.11; H, 7.19; S, 16.94.Found: C, 56.75; H, 7.24; S, 16.84.

EXAMPLE 4
4—[[2-[[3,5-bis(1,1-dimethylethyl)-4-hydroxyphenyl]-thio]ethyl]thio]acetic acid

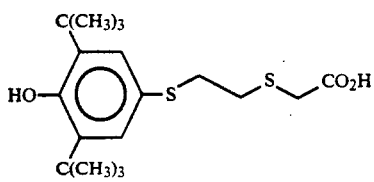

The title compound of Example 3 (0.90 g) was dissolved in water (40ml) acidified with 10% hydrochloric acid and extracted into ethyl acetate (2×50 ml). The combined extracts were dried over sodium sulfate, filtered and concentrated using a rotary evaporator to give an oil. The oil was crystallized from hexane to give the title compound, m.p. ca . 86° C.

Analysis calc. for $C_{18}H_{28}O_3S_2$ (356.54):Calc.: C, 60.64; H, 7.92; S, 17.98.Found: C, 60.93; H, 7.87; S, 17.81.

EXAMPLE 5

The title compound of Example 4 was also prepared by the procedure of Example 3 without the isolation of the sodium salt. The ethyl acetate solution containing the sodium salt was treated with ten percent hydrochloric acid, stirred for thirty minutes and the layers were separated. The organic layer was dried over sodium sulfate, filtered and concentrated with a rotary evaporator to give a solid which was recrystallized from hexane.

Analysis calc. for $C_{18}H_{28}O_3S_2$ (356.54):Calc.: C, 60.64; H, 7.92; S, 17.98.Found: C, 60.73; H, 7.84; S, 17.92.

EXAMPLE 6
6—2,6-bis(1,1-dimethylethyl)-4-[(2-hydroxy-1-methylpropyl)thio]phenol

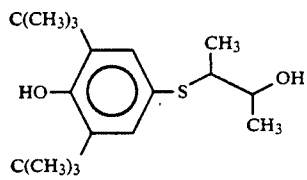

2,6-bis(1,1-Dimethylethyl)-4-mercaptophenol (18.2 g, 0.076 mole) was added to a solution of sodium ethoxide freshly prepared from sodium (3.5 g, 0.15 mole) in ethyl alcohol (100 ml) and stirred for 1 hour. After cooling to 5° C. with an ice bath, trans-2,3-epoxybutane (5.0 g, 0.069 mole) was added and the ice bath removed. After stirring for 5.5 hours the reaction mixture was poured into ten percent hydrochloric acid (50 ml). The ethyl alcohol was removed using a rotary evaporator and the aqueous residue extracted with ethyl acetate (2×75 ml). The extracts were combined, dried over sodium sulfate, filtered, and concentrated to an orange oil. The product was purified by chromatography on silica to give a yellow solid which was recrystallized from hexane to give a white solid, m.p. ca . 73° C.

Analysis calc. for $C_{18}H_{30}O_2S$ (310.5):Calc.: C, 69 63; H, 9.74; S, 10.33.Found: C, 69.75; H, 9.60; S, 10.35.

EXAMPLE 7
7—2,6-bis(1,1-dimethylethyl)-4-[(2-hydroxyethyl)thio]phenol

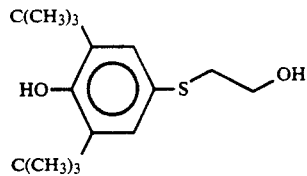

Triethylamine (0.42 g, 0.0042 mole), 2-bromoethanol (0.52 g, 0.0044 mole) and the title compound of Example 2 (1.0 g, 0.0042 mole) were stirred in methylene chloride (50 ml) for 20 hours. The reaction was condensed and ethyl acetate (25 ml) added to the residue. After filtering the white solid the filtrate was concentrated and the product purified by chromatography on silica, m.p. ca . 66° C.

Analysis calc. for $C_{16}H_{26}O_2S$ (282.4):Calc.: C, 68.04; H, 9.28; S, 11.35.Found: C, 67.98; H 9.20; S, 11.24.

EXAMPLE 8
8—[2-[[3,5-bis(1,1-dimethylethyl)-4-hydroxyphenyl]thio]ethoxy]acetic acid

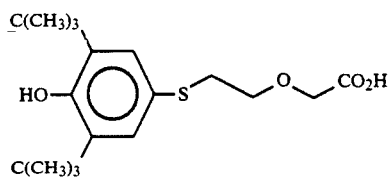

Chloroacetic acid (1.88 g) was added to a solution of the product of Example 7 (5.64 g) in tert-butyl alcohol. Potassium tert-butoxide (8.96 g) was added and the mixture refluxed for 22 hours. The reaction was made basic with 5% sodium bicarbonate and extracted with ethyl ether (3×50 ml). The NaHCO3 extracts were acidified to about pH 2 with 1N HCl and extracted 3 times with ethyl ether (100 ml). The combined organic extracts were washed twice with water, twice with saturated brine, dried over sodium sulfate and the solvent removed using a rotary evaporator to give the impure product. The product was purified by chromatography on silica, m.p. ca . 86° C.

Analysis calc. for $C_{18}H_{28}O_4S$ (340.47):Calc.: C, 63 50; H, 8.29; S, 9.42. Found: C, 63.52; H, 8.02; S, 9.46.

EXAMPLE 9
9—2S*-[[3,5-bis(1,1-dimethylethyl)-4-hydroxyphenyl]-thio]-1R*-methylpropoxy]acetic acid

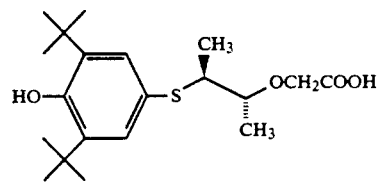

Starting with the 2,6-bis (1,1-dimethylethyl)-4-[(2-hydroxy-1-methylpropyl)thio]phenol of Example 6 and using the method of Example 8 gave the title compound, m.p. ca . 89°-92° C.; Mass Spec. 368 (M+).

EXAMPLE 10

10—(±)2,6-bis(1,1-dimethylethyl)-4-[(2S*-hydroxy-1R*-methylpropyl)thio]phenol

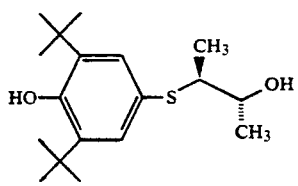

An argon-purged vessel was charged with 54 L of anhydrous methanol which was then purged with argon for 5 min. About 12 L of methanol was distilled off at atmospheric pressure, and the remaining methanol was transferred to pressure cans under argon. The dry, argon-purged vessel was charged with 3.03 kg of sodium methoxide followed by 29.7 kg of methanol from the pressure cans. The mixture was stirred for 10 min, and 6.7 kg of 2,6-bis(1,1-dimethylethyl)-4-mercaptophenol was added to small portions under argon. The mixture was stirred for 1 h at room temperature and cooled to 0° C. at which point 2.23 kg of trans-2,3-epoxybutane was added followed by a 2.7 kg methanol rinse. The mixture was stirred at 0° C. for 4 h and then at less than 25° C. for 16 h. When the reaction was complete as indicated by thin layer chromatography, the reaction mixture was added to 59 L of 1N hydrochloric acid, and the aqueous solution was extracted twice with a total of 89 L of ethyl acetate. The combined organic phase was washed once with 34 L of dilute aqueous sodium chloride solution and once with 13 L of saturated aqueous sodium chloride solution. The organic phase was dried over 3.5 kg of anhydrous magnesium sulfate and filtered. The solvent was removed by distillation under reduced pressure. The crude product was dissolved in 6.7 L of refluxing n-hexane, and the solution was cooled to 5° C. The solid was collected by filtration, washed with cold (about 0° C.) n-hexane and dried at 50° C. in a vacuum oven to give 7.44 kg (85% of theory) of (±)2,6-bis(1,1-dimethylethyl)-4-[(2S*-hydroxy-1R*-methylpropyl)thio]phenol.

EXAMPLE 11—(±)[2S*-[[3,5-bis(1-dimethylethyl)-4-hydroxyphenyl]thio]-1R*-methylpropoxy]acetic acid

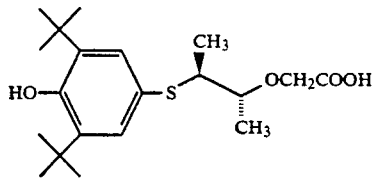

A dry, argon purged vessel was charged with 1.6 kg of sodium hydride (60% dispersion in oil) which was then washed three times with a total of 21 kg of n-heptane. The reaction vessel was cooled to −20° C., and 41 L of dry tetrahydrofuran (THF) was added under argon. A solution of 4.0 kg of (±)2,6-bis(1,1-dimethylethyl)-4[(2S*-hydroxy-1R*-methylpropyl)-thio]phenol in 16 L of tetrahydrofuran was added slowly to the sodium hydride suspension, and the mixture was warmed to 0°-5° C. and stirred for 1.5 h. The tetrahydrofuran was removed at reduced pressure, and 12 L of dimethyl sulfoxide was added under argon. A solution of 1.9 kg of sodium chloroacetate in 40 L of dimethyl sulfoxide was added, and the mixture was stirred at room temperature for approximately 15 h. When the reaction was complete, as indicated by thin layer chromatography, the reaction mixture was added to approximately 178 L of water at 5°-10° C., and the aqueous solution was extracted twice with a total of 60 L of n-heptane. The aqueous phase was acidified with 14 L of 4N hydrochloric acid and extracted three times with a total of 95 L of ethyl acetate. The combined organic phase was washed twice with a total of 74 L of water and once with 20 L of saturated aqueous sodium chloride solution. The organic phase was dried over 2.0 kg of anhydrous magnesium sulfate, filtered, and the solvent was removed by distillation under reduced pressure. The product was dissolved in 40 L of refluxing n-hexane, and the solution was cooled to room temperature. The product was collected by filtration, washed twice with a total of 20 L of n-hexane and dried at room temperature in a vacuum oven to give 4.27 kg (90% of theory) of (±)[2S*-[[3,5-bis(1,1-dimethyl-ethyl)-4-hydroxyphenyl]thio]-1R*-methylpropoxy]acetic acid (first crop). The hexane filtrate was concentrated under vacuum to give an additional 0.23 kg of product (4.80% of theory).

EXAMPLE 12

12—(±)[2S*-[[3,5-bis(1,1-dimethylethyl)-4-hydroxyphenyl]sulfinyl]-1R*-methylpropoxy]acetic acid

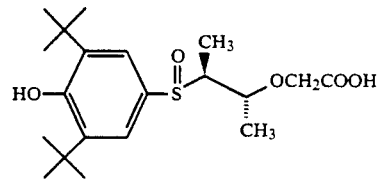

m-Chloroperoxybenzoic acid (0.87 g, 0.0051 mole) was added to a cold (0° C.) solution of [2S*-[[3,5-bis(1,1-dimethylethyl)-4-hydroxyphenyl]thio]-1R*-methylpropoxy]acetic acid (1.5 g, 0.0041 mole) in methylene chloride (50 ml) and stirred for 4 hrs. After filtering, the filtrate was washed with a saturated solution of sodium thiosulfate (50 ml), dried over anyhydrous sodium sulfate, filtered and concentrated to an oily solid. The product was purified by silica gel chromatography and crystallized from ethyl acetate-hexane. The structure was supported by NMR, infrared spectrascopy and elemental analysis.

Analysis calcd. for $C_{20}H_{32}O_5S$: (m.w.=384.54).Theory: C, 62.47; H, 8.39; S, 8.34.Found: C, 62.16; H, 8.27; S, 8.00.

EXAMPLE 13

13—(±)[2S*-[[3,5-bis(1,1-dimethylethyl)-4-hydroxyphenyl]sulfonyl]-1R*-methylpropoxy]acetic acid

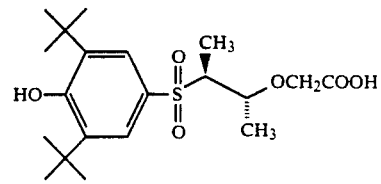

m-Chloroperoxybenzoic acid (1.75 g, 0.0107 mole) was added to a cold (0° C.) solution of [2S*-[[3,5-bis(1,1-dimethylethyl)-4-hydroxyphenyl]thio]-1R*-methylpropoxy]acetic acid (1.5 g, 0.0041 mole) in methylene chloride (50 ml) and stirred for 4 hrs. After filtering, the filtrate was washed with a saturated solution of sodium thiosulfate (50 ml), dried over anyhydrous sodium sulfate, filtered and concentrated to an oily solid. The product was purified by silica gel chromatography and crystallized from ethyl acetate-hexane. The structure was supported by NMR, infrared spectrascopy and elemental analysis.

Analysis calcd. for $C_{20}H_{37}O_6S$: (m.w.=400.54).Theory: C, 59.98; H, 8.05; S, 8.01.Found: C, 59.89; H, 7.82; S, 7.94.

EXAMPLE 14

14—[2S*-[[3,5-bis(1,1-dimethylethyl)-4-hydroxyphenyl]thio]-1R*-methylpropyl][1R-(1-naphthalenyl)ethyl]carbamate or
[2R*-[[3,5-bis(1,1-dimethylethyl)-4-hydroxyphenyl]thio]-1S*-methylpropyl][1R-(1-naphthalenyl)ethyl]carbamate

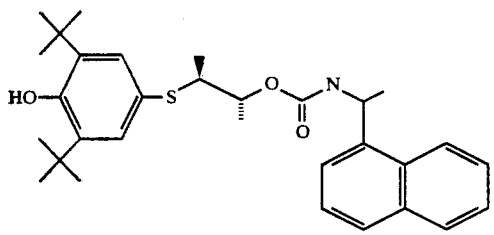

OR

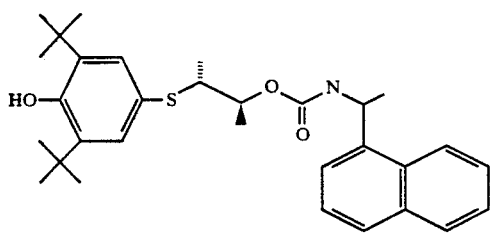

2,6-bis(1,1-Dimethylethyl)-4-[(2-hydroxy-1-methylpropyl)thio]phenol (6.3 g, 0.0203 mole) and (R)-(1)-1-(1-napthyl)ethyl isocyanate were heated in toluene (75 ml) for 20 hrs. The carbamates were separated by silica gel chromatography (toluene) to give Isomer A (first off) and Isomer B (last off).

EXAMPLE 15

15—2,6-bis(1,1-dimethylethyl)-4-[(2S*-hydroxy-1R*-methylpropyl) thio]phenol or
2,6-bis(1,1-dimethylethyl)-4-[(2R*-hydroxy-1S*-methylpropyl) thio]phenol

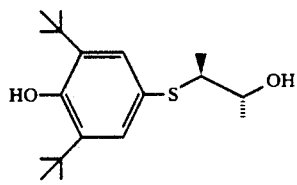

OR

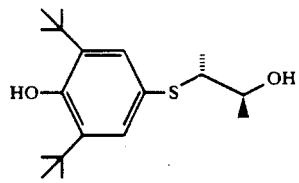

Trichlorosilane (1.02 g, 0.00752 mole) was added dropwise by syringe to a stirring solution of Isomer A (from Example 14) (1.80 g, 0.00375 mole) and triethylamine (0.75 g, 0.00757 mole) in benzene (25 ml) and stirred at room temperature for 28 hrs. The reaction was poured into a mixture of ethyl acetate (50 ml) and saturated ammonium chloride (25 ml), stirred for min. and the layers were separated. The organic layer was dried over anhydrous sodium sulfate, filtered and concentrated to an oil. The product was purified by silica gel chromatography and the structure verified by NMR.

EXAMPLE 16

16—2,6-bis(1,1-dimethylethyl)-4-[(2S*-hydroxy-1R*-methylpropyl) thio]phenol or
2,6-bis(1,1-dimethylethyl)-4-[(2R*-hydroxy-1S*-methylpropyl) thio]phenol

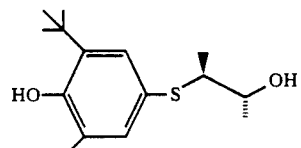

OR

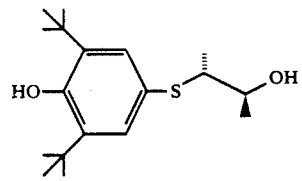

Trichlorosilane (0.79 g, 0.00584 mole) was added dropwise by syringe to a stirring solution of Isomer B (from Example 14) (1.40 g, 0.00292 mole) and triethylamine (0.59 g, 0.00584 mole) in benzene (40 ml) and stirred at room temperature for 28 hrs. The solution was poured into a mixture of hexane (100 ml) and saturated ammonium chloride (15 ml), stirred for 15 min., and the layers were separated. The organic layer was dried over anhydrous sodium sulfate, filtered and concentrated to an oil. The product was purified by silica gel chromatography. The structure was supported by NMR.

EXAMPLE 17—Preparation of (−) Enantiomer: (−)[2S*-[[3,5-bis(1,1-dimethylethyl)-4-hydroxyphenyl]thio]-1R*-methylpropoxy]acetic acid

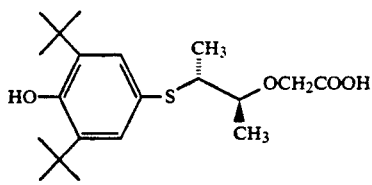

OR

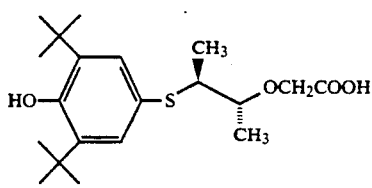

The compound of Example 15 (Enantiomer A) (0.36 g, 0.00116 mole) in dimethyl sulfoxide (1.5 ml) was added to a mixture of sodium hydride (0.086 g, 0.00360 mole) in dimethyl sulfoxide (1 ml). After stirring for 1 hr. at room temperature, chloroacetic acid, sodium salt (0.162 g, 0.00139 mole) was added and the reaction mixture was stirred for 20 hrs. The reaction mixture was poured into water (10 ml) and washed with hexane (25 ml). The aqueous layer was acidified with 10% hydrochloric acid, and the product extracted into ethyl acetate. The ethyl acetate layer was washed with water ml), dried over anhydrous sodium sulfate, filtered and concentrated to an oil. The product was purified by silica gel chromatography. The structure was supported by NMR, infrared ($[\alpha]_{365}^{25} - 174°$, CHCl₃) spectroscopy, optical rotation and elemental analysis.

Analysis calculated for $C_{20}H_{32}O_4S$: (m.w. = 368.5). Theory: C, 65.18; H, 8.75. Found: C, 65.33; H, 9.09.

EXAMPLE 18—Preparation of (+) Enatiomer: (+)[2S*-[[3,5-bis(1,1-dimethylethyl)-4-hydroxyphenyl]thio]-1R*-methylpropoxy]acetic acid

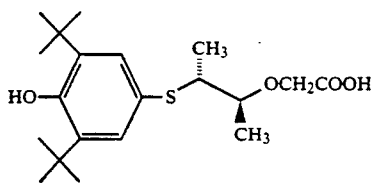

OR

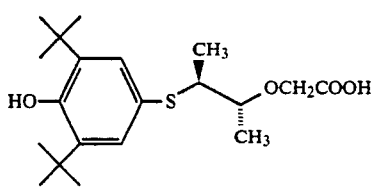

The compound of Example 16 (Enantiomer B) (0.19 g, 0.000613 mole) in dimethyl sulfoxide (DMSO) (2.5 ml) was added to a mixture of sodium hydride (0.045 g, 0.00180 mole) in dimethyl sulfoxide (1.5 ml). After stirring for 1 hr. at room temperature, chloroacetic acid, sodium salt (0.086 g, 0.000736 mole) was added and the reaction mixture was stirred for 64 hrs. The reaction mixture was poured into water (10 ml) and washed with hexane (25 ml). The aqueous layer was acidified with 10% hydrochloric acid, and the product extracted into ethyl acetate. The ethyl acetate layer was washed with water (10 ml), dried over anhydrous sodium sulfate, filtered and concentrated to an oil. The product was purified by silica gel chromatography. The structure was supported by NMR, infrared spectroscopy, optical rotation ($[\alpha]_{365}^{25} + 168°$, CHCl₃) and elemental analysis.

Analysis calculated for $C_{20}H_{32}O_4S$: (m.w. = 368.5). Theory: C, 65.18; H, 8.75. Found: C, 65.03; H, 8.95.

What is claimed is:

1. A method of inhibiting superoxide generation in a mammal which comprises administering to a mammal in need of such treatment an amount of a compound of the Formula I

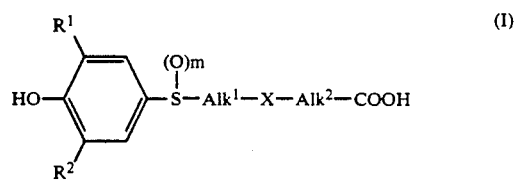

wherein $R^1$ and $R^2$ are the same or different and independently represent tert-alkyl or phenyl; $Alk^1$ represents straight or branched chain alkylene of 1 to 10 carbon atoms, X represents sulfur or oxygen, $Alk^2$ represents straight or branched chain alkylene of 1 to 4 carbon atoms; and m is 0, 1 or 2; or a pharmaceutically acceptable salt or stereoisomer or geometric isomer thereof, which is effective to inhibit superoxide generation.

2. A method according to claim 1 of inhibiting superoxide generation in a mammal which comprises administering to a mammal in need of such treatment an amount of a compound of the formula

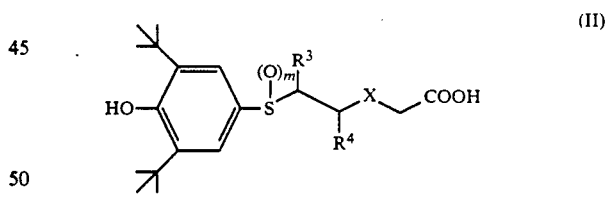

wherein $R^3$ and $R^4$ are alike or different and are hydrogen or alkyl of 1 to 4 carbon atoms, X is sulfur or oxygen, and m is 0, 1 or 2; or a pharmaceutically acceptable salt or stereoisomer or geometric isomer thereof which is effective to inhibit superoxide generation.

3. A method according to claim 1 wherein said compound has the formula

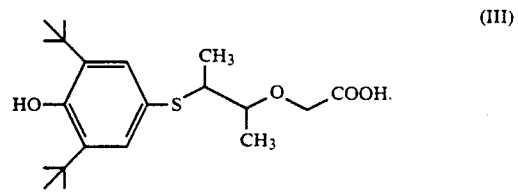

4. A method according to claim 1 wherein said compound is (±)[2S*-[[3,5-bis(1,1-dimethylethyl)-4-hydroxyphenyl]thio]-1R*-methylpropoxy]acetic acid.

5. A method according to claim 1 wherein said compound is [[2-[[3,5-bis(1,1-dimethylethyl)-4-hydroxyphenyl]thio]ethyl]thio]acetic acid.

6. A method according to claim 1 wherein said compound is (±)[2S*-[[3,5-bis(1,1-dimethylethyl)-4-hydroxyphenyl]sulfinyl]-1R*-methylpropoxy]acetic acid.

7. A method according to claim 1 wherein said compound is (±)[2S*-[[3,5-bis(1,1-dimethylethyl)-4-hydroxyphenyl]sulfonyl]-1R*-methylpropoxy]acetic acid.

8. A method according to claim 1 wherein said compound is (−)[2S*-[[3,5-bis(1,1-dimethylethyl)-4-hydroxyphenyl]thio]-1R*-methylpropoxy]acetic acid.

9. A method according to claim 1 wherein said compound is (+)[2S*-[[3,5-bis(1,1-dimethylethyl)-4-hydroxyphenyl]thio]-1R*-methylpropoxy]acetic acid.

* * * * *

UNITED STATES PATENT AND TRADEMARK OFFICE
CERTIFICATE OF CORRECTION

PATENT NO. : PATENT NO: 5,064,860          Page 1 of 3
DATED      : DATED: November 12, 1991
INVENTOR(S): INVENTOR(S): Richard A. Mueller, et al.

It is certified that error appears in the above-identified patent and that said Letters Patent is hereby corrected as shown below:

Column 2, Line 35, reading "Ar-Q-Q-S-R" should read -- Ar-Q-A-S-R --.

Column 6, Line 15, reading "nuetropil" should read -- neutrophil --.

Column 6, Line 15, reading "suproxide" should read -- superoxide --.

Column 6, Line 40, reading "a ml" should read -- a 15 ml --.

Column 7, Line 40, reading "1—3,5-bis" should read -- 3,5-bis --.

Column 8, Line 4, reading "N, 5 32" should read -- N, 5.32 --.

Column 8, Line 7, reading "2—2,6-bis" should read -- 2,6-bis --.

Column 8, Line 33, reading "3—[[2-" should read -- [[2- --.

Column 9, Line 2, reading "4—[[2-" should read -- [[2- --.

Column 9, Line 40, reading "6—2,6-bis" should read -- 2,6-bis --.

Column 9, Line 67, reading "C, 69 63;" should read -- C, 69.63; --.

Column 10, Line 1, reading "7—2,6-bis" should read -- 2,6-bis --.

UNITED STATES PATENT AND TRADEMARK OFFICE
CERTIFICATE OF CORRECTION

PATENT NO. : 5,064,860

DATED : November 12, 1991

INVENTOR(S) : Richard A. Mueller, et al.

It is certified that error appears in the above-identified patent and that said Letters Patent is hereby corrected as shown below:

Column 10, Line 23, reading "H 9.20;" should read -- H, 9.20; --.

Column 10, Line 26, reading "8—[2-" should read -- [2- --.

Column 10, Line 50, reading "C, 63 50;" should read -- C, 63.50; --.

Column 10, Line 53, reading "9—2S*-" should read -- 2S*- --.

Column 11, Line 2, reading "10—(±)2,6-" should read -- (±)2,6- --.

Column 11, Line 23, reading "added to small" should read -- added in small --.

Column 11, Line 43, reading "(2S*-hydroxy-1R-" should read -- (2S*-hydroxy-1R*- --.

Column 11, Line 46, reading "(1-dimethylethyl)" should read -- (1,1-dimethylethyl) --.

Column 12, Line 29, reading "12—(±)[2S*-" should read -- (±)[2S*- --.

Column 12, Line 57, reading "13—(±)[2S*-" should read -- (±)[2S*- --.

Column 13, Line 18, reading "14—[2S*-" should read -- [2S*- --.

UNITED STATES PATENT AND TRADEMARK OFFICE
CERTIFICATE OF CORRECTION

PATENT NO. : 5,064,860

DATED : November 12, 1991

INVENTOR(S) : Richard A. Mueller, et al.

It is certified that error appears in the above-identified patent and that said Letters Patent is hereby corrected as shown below:

Column 13, Line 55, reading "15—2,6-bis" should read -- 2,6-bis --.

Column 14, Line 21, reading "stirred for min." should read -- stirred for 15 min. --.

Column 14, Line 29, reading "16—2,6-bis" should read -- 2,6-bis --.

Column 15, Line 34, reading "water ml), should read -- water (10 ml), --.

Column 15, Line 37, reading "$([\alpha]_{365}^{25}$" should be -- $([\alpha]_{365}^{25}$ --.

Column 16, Line 11, reading "$([\alpha]_{365}^{25}$" should be -- $([\alpha]_{365}^{25}$ --.

Signed and Sealed this

Thirty-first Day of August, 1993

Attest:

BRUCE LEHMAN

*Attesting Officer*  *Commissioner of Patents and Trademarks*